United States Patent [19]

Zanno et al.

[11] Patent Number: 4,678,674

[45] Date of Patent: Jul. 7, 1987

[54] SWEETENING WITH L-AMINODICARBOXYLIC ACID AMIDES

[75] Inventors: Paul R. Zanno, Nanuet; Ronald E. Barnett, Suffern; Glenn M. Roy, Garnerville, all of N.Y.

[73] Assignee: General Foods Corporation, White Plains, N.Y.

[21] Appl. No.: 919,907

[22] Filed: Oct. 16, 1986

Related U.S. Application Data

[62] Division of Ser. No. 795,377, Nov. 5, 1985, which is a division of Ser. No. 723,600, Apr. 15, 1985, Pat. No. 4,572,799.

[51] Int. Cl.$^4$ .............................................. A23L 1/236
[52] U.S. Cl. .................................................. 426/548
[58] Field of Search ........................................ 426/548

[56] References Cited

U.S. PATENT DOCUMENTS 4,572,799  2/1986  Zanno et al. ................ 260/112.5 R Primary Examiner—Joseph Golian
Attorney, Agent, or Firm—Linn I. Grim; Thomas A. Marcoux; Daniel J. Donovan

[57] ABSTRACT

Sweeteners of the formula:

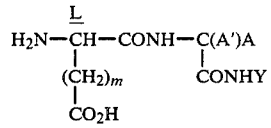

and food-acceptable salts thereof, where the substituents are disclosed herein.

25 Claims, No Drawings

SWEETENING WITH L-AMINODICARBOXYLIC ACID AMIDES

This is a division of application Ser. No. 795,377, filed Nov. 5, 1985, which is a division of application Ser. No. 723,600, filed Apr. 15, 1985, now U.S. Pat. No. 4,572,799, issued Feb. 25, 1986.

FIELD OF THE INVENTION

This invention relates to a novel group of compounds and more particularly to a novel group of compounds particularly well suited as sweeteners in edible foodstuff.

DESCRIPTION OF THE PRIOR ART

Sweetness is one of the primary taste cravings of both animals and humans. Thus, the utilization of sweetening agents in foods in order to satisfy this sensory desire is well established.

Naturally occuring carbohydrate sweeteners such as sucrose, are still the most widely used sweetening agents. While the naturally occurring carbohydrates, i.e., sugars, generally fulfill the requirements of sweet taste, the abundant usage thereof does not occur without deleterious consequence, e.g., high caloric intake and nutritional imbalance. In fact, oftentimes the level of these sweeteners required in foodstuffs is far greater than the level of the sweetener that is desired for economic, dietetic or other functional consideration.

In an attempt to eliminate the disadvantages concomitant with natural sweeteners, considerable research and expense have been devoted to the production of artificial sweeteners, such as for example, saccharin, cyclamate, dihydrochalcone, aspartame, etc. While some of these artificial sweeteners satisfy the requirements of sweet taste without caloric input, and have met with considerable commercial success, they are not, however, without their own inherent disadvantages. For example, many of these artificial sweeteners have the disadvantages of high cost, as well as delay in the perception of the sweet taste, persistent lingering of the sweet taste, and very objectionable bitter, metallic aftertaste when used in food products.

Since it is believed that many disadvantages of artificial sweeteners, particularly aftertaste, is a function of the concentration of the sweetener, it has been previously suggested that these effects could be reduced or eliminated by combining artificial sweeteners such as saccharin, with other ingredients such as aspartame or natural sugars, such as sorbitol, dextrose, maltose, etc. These combined products, however, have not been entirely satisfactory either. Some U.S. Patents which disclose sweetener mixtures include for example, U.S. Pat. No. 4,228,198; U.S. Pat. No. 4,158,068; U.S. Pat. No. 4,154,862; and U.S. Pat. No. 3,717,477.

Accordingly, much work has continued in an attempt to develop and identify compounds that have a sweet taste and which will satisfy the need for better lower calorie sweeteners. Search continues for sweeteners that have intense sweetness, that is, deliver a sweet taste at low use levels and which will also produce enough sweetness at low levels to act as sole sweetener for most sweetener applications. Furthermore, the sweeteners sought must have good temporal and sensory qualities. Sweeteners with good temporal qualities produce a time-intensity sweetness response similar to natural sweeteners without lingering. Sweeteners with good sensory qualities lack undesirable off tastes and aftertaste. Furthermore, these compounds must be economical and safe to use.

In U.S. Pat. No. 3,798,204, L-aspartyl-O-t-butyl-L-serine methyl ester and L-aspartyl-O-t-amyl-L-serine methyl ester are described as sweet compounds having significant sweetness.

In U.S. Pat. No. 4,448,716 metal complex salts of dipeptide sweetners are disclosed. In the background of this patent a generic formula is described as an attempt to represent dipeptide sweetners disclosed in five prior patents: U.S. Pat. No. 3,475,403; U.S. Pat. No. 3,492,131; Republic of South Africa Pat. No. 695,083 published July 10, 1969; Republic of South Africa Pat. No. 695,910 published Aug. 14, 1969; and German Pat. No. 2,054,554. The general formula attempting to represent these patents is as follows:

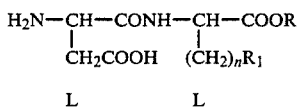

wherein R represents the lower alkyls, lower alkylaryls and cycloalkyls, n stands for integers 0 through 5, $R_1$ represents (a) phenyl group, (b) lower alkyls, (c) cycloalkyls, (d) $R_2$.

Where $R_2$ is hydroxy, lower alkoxy, lower alkyl, halogen, (e) $S(O)_m$ (lower alkyl) where m is 0, 1 or 2 and provided n is 1 or 2, (f) $R_3$.

Where $R_3$ represents an hydroxy or alkoxy and (g) single or double unsaturated cycloalkyls with up to eight carbons. These compounds also are not entirely satisfactory in producing a high quality sweetness or in producing a sweet response at lower levels of sweetener.

Dipeptides of aspartyl-cysteine and aspartyl-methionine methyl esters are disclosed by Brussel, Peer and Van der Heijden in *Chemical Senses and Flavour*, 4, 141–152 (1979) and in *Z. Lebensm. Untersuch-Forsch.*, 159, 337–343 (1975). The authors disclose the following dipeptides:

α-L-Asp-L-Cys(Me)-OMe

α-L-Asp-L-Cys(Et)-OMe

α-L-Asp-L-Cys(Pr)-OMe

α-L-Asp-L-Cys(i-Pr)-OMe

α-L-Asp-L-Cys(t-But)-OMe

α-L-Asp-L-Met-OMe

In U.S. Pat. No. 4,399,163 to Brennan et al., sweeteners having the following formulas are disclosed:

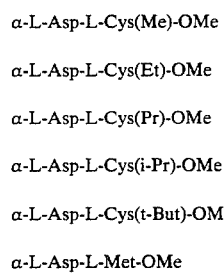

and physiologically acceptable cationic and acid addition salts thereof wherein $R^a$ is $CH_2OH$ or $CH_2OCH_3$;

R is a branched member selected from the group consisting of fenchyl, diisopropylcarbinyl, d-methyl-t-butylcarbinyl, d-ethyl-t-butyl-carbinyl, 2-methylthio-2,4-dimethylpentan-3yl, di-t-butyl-carbinyl,

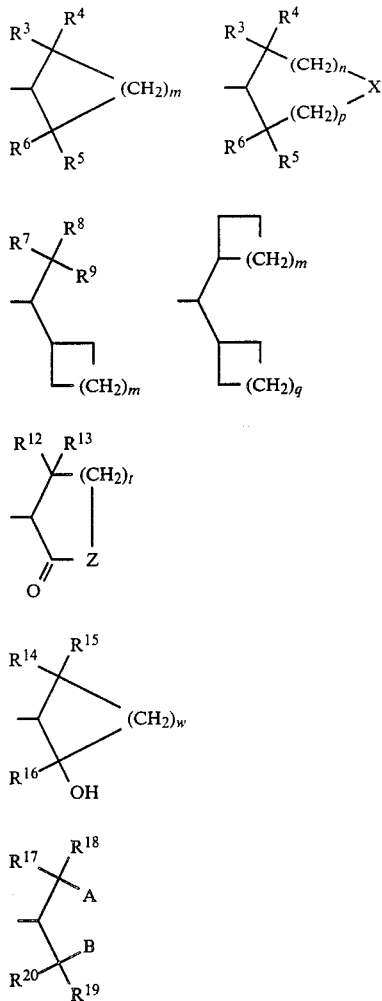

In a related patent, U.S. Pat. No. 4,411,925, Brennan, et al. disclose compounds of the above general formula with R being defined hereinabove, except $R^a$ is defined as methyl, ethyl, n-propyl or isopropyl.

U.S. Pat. No. 4,375,430 to Sklavounos discloses dipeptide sweeteners which are aromatic sulfonic acid salts of L-aspartyl-D-alaninoamides or L-aspartyl-D-serinamides.

European Patent Application No. 95772 to Tsau describe aspartyl dipeptide sweeteners of the formula:

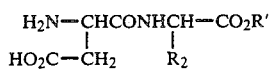

wherein R' is alkyl of 1 to 6 carbons, and $R_2$ is phenyl, phenylakylenyl or cyclohexylalkenyl, wherein the alkenyl group has 1 to 5 carbons. Closely related is U.S. Pat. No. 4,439,460 to Tsau, et al. which describes dipeptide sweeteners of the formula:

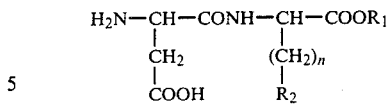

wherein n is an integer from 0 to 5, and $R_1$ is an alkyl, alkylaryl or alicyclic radical. Similar such compounds are described in many related patents, the major difference being the definition of $R_2$.

In U.S. Pat. No. 3,978,034 to Sheehan, et al., $R_2$ is defined as cycloalkenyl or phenyl. U.S. Pat. No. 3,695,898 to Hill defines $R_2$ as a mono- or a di-unsaturated alicyclic radical. Haas, et al. in U.S. Pat. No. 4,029,701 define $R_2$ as phenyl, lower alkyl or substituted or unsubstituted cycloalkyl, cycloalkenyl or cycloalkdienyl, or $S(O)_m$ lower alkyl provided that n is 1 or 2 and m is 0 or 2. Closely related are U.S. Pat. Nos. 4,448,716, 4,153,737, 4,031,258, 3,962,468, 3,714,139, 3,642,491, and 3,795,746.

U.S. Pat. No. 3,803,223 to Mazur, et al. describe dipeptide sweeteners and anti-inflammatory agents having the formula:

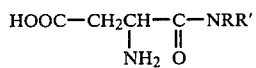

wherein R is hydrogen or a methyl radical and R' is a radical selected from the group consisting of alkyl, or

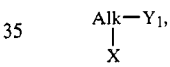

wherein Alk is a lower alkylene radical, X is hydrogen or hydroxy, and Y is a radical selected from the group consisting of cyclohexyl, naphthyl, furyl, pyridyl, indolyl, phenyl and phenoxy.

Goldkamp, et al. in U.S. Pat. No. 4,011,260 describe sweeteners of the formula:

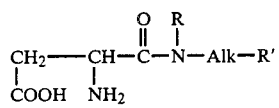

wherein R is hydrogen or a lower alkyl radical, Alk is a lower alkylene radical and R' is a carbocyclic radical. Closely related is U.S. Pat. No. 3,442,431.

U.S. Pat. No. 4,423,029 to Rizzi describes sweeteners of the formula:

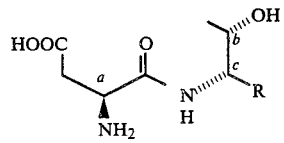

wherein R is $C_4$–$C_9$ straight, branched or cyclic alkyl, and wherein carbons a, b and c have the (S) configuration.

European Patent Application No. 48,051 describes dipeptide sweeteners of the formula:

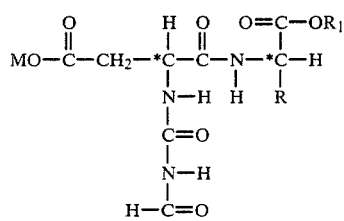

wherein
M represents hydrogen, ammonium, alkali or alkaline earth,
R represents

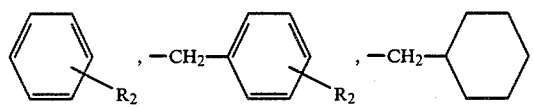

$R_1$ represents methyl, ethyl, propyl,
$R_2$ represents —OH, or $OCH_3$,
* signifies an L-optical configuration for this atom.

German Patent Application No. 7259426 discloses L-aspartyl-3-fenchylalanine methyl ester as a sweetening agent.

U.S. Pat. No. 3,971,822 to Chibata, et al., disclose sweeteners having the formula:

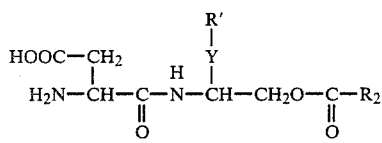

wherein R' is hydrogen or hydroxy, $R_2$ is alkyl of one to five carbon atoms, alkenyl of two to three carbon atoms, cycloalkyl of three to five carbon atoms or methyl cycloalkyl of four to six carbon atoms and Y is alkylene of one to four carbon atoms.

U.S. Pat. No. 3,907,366 to Fujino, et al. discloses L-aspartyl-aminomalonic acid alkyl fenchyl diester and its' physiologically acceptable salts as useful sweeteners. U.S. Pat. No. 3,959,245 disclose the 2-methyl cyclohexyl analog of the abovementioned patent.

U.S. Pat. No. 3,920,626 discloses N-αL-aspartyl derivatives of lower alkyl esters of O-lower-alkanoyl-L-serine, β-alanine, α-aminobutyric acid and D-β-aminobutyric acid as sweeteners.

Miyoshi, et al. in *Bulletin of Chemical Society of Japan*, 51, p. 1433-1440 (1978) disclose compounds of the following formula as sweeteners:

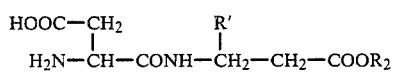

wherein R' is H, $CH_3$, $CO_2CH_3$, or benzyl and $R_2$ is lower alkyl or unsubstituted or substituted cycloalkyl.

European Patent Application No. 128,654 describes gem-diaminoalkane sweeteners of the formula:

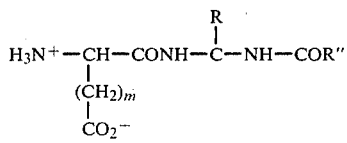

wherein m is 0 or 1, R is lower alkyl (substituted or unsubstituted), R' is H or lower alkyl, and R" is a branched alkyl, alkylcycloalkyl, cycloalkyl, polycycloalkyl, phenyl, or alkyl-substituted phenyl, and physically acceptable salts thereof.

U.S. Pat. No. 3,801,563 to Nakajima, et al. disclose sweeteners of the formula:

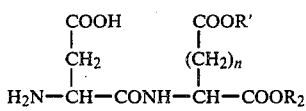

wherein R' is a branched or cyclic alkyl group of 3 to 8 carbon atoms, $R_2$ is a lower alkyl group of 1 to 2 carbon atoms and n is a integer of 0 or 1.

European Patent Application No. 34,876 describes amides of L-aspartyl-D-amino acid dipeptides of the formula:

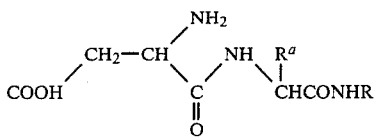

wherein $R^a$ is methyl, ethyl, n-propyl or isopropyl and R is a branched aliphatic, alicyclic or heterocyclic member which is branched at the alpha carbon atom and also branched again at one or both of the beta carbon atoms. These compounds are indicated to be of significant sweetness.

In the *Journal of Medicinal Chemistry*, 1984, Vol. 27, No. 12, pp. 1663-8, are described various sweetener dipeptide esters, including L-aspartyl-α-aminocycloalkane methyl esters.

The various dipeptide esters of the prior art have been characterized as lacking significant stability at low pH values and/or thermal stability. These characteristics have limited the scope of use of these sweeteners in food products which are of low pH values or are prepared or served at elevated temperatures.

Accordingly, it is desired to find compounds that provide quality sweetness when added to foodstuffs or pharmaceuticals at low levels and thus eliminate or greatly diminish the aforesaid disadvantages associated with prior art sweeteners.

SUMMARY OF THE INVENTION

The present new compounds are amides of certain α-aminodicarboxylic acids and β-aminoamides which are low calorie sweeteners that possess a high order of sweetness with pleasing taste and higher stability at acid pH and elevated temperatures compared to known dipeptide sweeteners.

This invention provides new sweetening compounds represented by the formula:

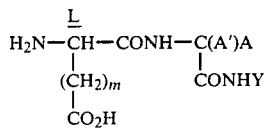

wherein
- A is alkyl containing 1-3 carbon atoms or $CO_2R$ where R is alkyl containing 1-3 carbon atoms;
- A' is hydrogen or alkyl containing 1-3 carbon atoms; with the proviso that when A is alkyl, A' is alkyl;
- A and A' taken together with the carbon atom to which they are attached form cycloalkyl containing 3-4 carbon atoms;
- Y is $-(CHR_2)_n-R_1$ or $-CHR_3R_4$;
- $R_1$ is cycloalkyl, cycloalkenyl, lower alkyl substituted cycloalkyl or cycloalkenyl, bicycloalkyl, bicycloalkenyl or tricycloalkyl containing up to 10 ring carbon atoms and up to a total of 12 carbon atoms;
- $R_2$ is H or alkyl containing 1-4 carbon atoms;
- $R_3$ and $R_4$ are each cycloalkyl containing 3-4 ring carbon atoms;
- n=0 or 1; and
- m=0 or 1;
and food-acceptable salts thereof.

DESCRIPTION OF THE PREFERRED EMBODIMENTS

In accordance with the present invention, the preferred compounds are those in which $R_1$ is an alkyl-substituted cycloalkyl or bicycloalkyl containing 5-7 ring carbon atoms and up to a total of 10 carbon atoms. Especially preferred are cycloalkyl substituted with at least one methyl group on the β and/or β' carbon atoms of the cycloalkyl ring. Particularly preferred cycloalkyls include cyclopropyl, cyclopentyl, and cyclohexyl and the preferred bicycloalkyl is fenchyl.

Also preferred are those compounds in which n=0. In those compounds in which n=1, $R_1$ is preferably a cyclopropyl group and $R_2$ is preferably tertiary butyl, isopropyl or cyclopropyl.

The groups representative of Y in the present new compounds include such groups as cycloalkyl, e.g., cyclobutyl, cyclopentyl, cyclohexyl, cycloheptyl, etc.; alkyl-substituted cycloalkyls, e.g., 1-methylcyclopentyl, 1-methylcyclohexyl, 1-methylcyclobutyl, 1-methylcycloheptyl, 1-ethylcyclobutyl, 1-ethylcyclopentyl, 1-ethylcycloheptyl, 1-ethylcyclohexyl, 1-isopropylcyclobutyl, 1-isopropylcyclopentyl, 1-isopropylcyclohexyl, 1-isopropylcycloheptyl, 1,2-dimethylcyclohexyl, 1,2-dimethylcyclopentyl, 1,2-dimethylcycloheptyl, 1,3-dimethylcyclohexyl, 1,3-dimethylcyclopentyl, 1,3-dimethylcycloheptyl, 1,4-dimethylcyclohexyl, 1,4-dimethylcycloheptyl, 2,3-dimethylcyclopentyl, 2,3-dimethylcyclohexyl, 2,3-dimethylcycloheptyl, 2,4-dimethylcyclopentyl, 2,4-dimethylcyclohexyl, 2,4-dimethylcycloheptyl, 2,5-dimethylcyclopentyl, 2,5-dimethylcyclohexyl, 2,5-dimethylcycloheptyl, 2,6-dimethylcyclohexyl, 2,6-dimethylcycloheptyl, 2,7-dimethylcycloheptyl, 3,4-dimethylcyclopentyl, 3,4-dimethylcyclohexyl, 3,4-dimethylcycloheptyl, 3,5-dimethylcyclopentyl, 3,5-dimethylcyclohexyl, 3,5-dimethylcycloheptyl, 4,5-dimethylcyclopentyl, 4,5-dimethylcyclohexyl, 4,5-dimethylcycloheptyl, 3,6-dimethylcyclohexyl, 3,6-dimethylcycloheptyl, 3,7-dimethylcycloheptyl, 4,6-dimethylcyclohexyl, 4,6-dimethylcycloheptyl, 4,7-dimethylcycloheptyl, 5,6-dimethylcyclohexyl, 5,6-dimethylcycloheptyl, 5,6-dimethylcycloheptyl, 5,7-dimethylcycloheptyl, 6,7-dimethylcycloheptyl, 2,2-dimethylcyclopentyl, 2,2-dimethylcyclohexyl, 2,2-dimethylcycloheptyl, 3,3-dimethylcyclopentyl, 3,3-dimethylcyclohexyl, 3,3-dimethylcycloheptyl, 4,4-dimethylcyclohexyl, 4,4-dimethylcycloheptyl, 2,2,3-trimethylcyclopentyl, 2,2,3-trimethylcyclohexyl, 2,2,3-trimethylcycloheptyl, 2,2,4-trimethylcyclopentyl, 2,2,4-trimethylcyclohexyl, 2,2,4-trimethylcycloheptyl, 2,2,5-trimethylcyclopentyl, 2,2,5-trimethylcyclohexyl, 2,2,5-trimethylcycloheptyl, 2,2,6-trimethylcyclohexyl, 2,2,6-trimethylcycloheptyl, 2,2,7-trimethylcycloheptyl, 1,2,2-trimethylcyclopentyl, 1,2,2-trimethylcyclohexyl, 1,2,2-trimethylcycloheptyl, 1,3,3-trimethylcyclopentyl, 1,3,3-trimethylcyclohexyl, 1,3,3-trimethylcycloheptyl, 1,4,4-trimethylcyclohexyl, 1,4,4-trimethylcyclopentyl, 3,3,4-trimethylcyclopentyl, 3,3,4-trimethylcyclohexyl, 3,3,4-trimethylcycloheptyl, 2,3,3-trimethylcyclopentyl, 2,3,3-trimethylcyclohexyl, 2,3,3-trimethylcycloheptyl, 2,4,4-trimethylcyclopentyl, 2,4,4-trimethylcyclohexyl, 2,4,4-trimethylcycloheptyl, 1,2,3-trimethylcyclopentyl, 1,2,3-trimethylcyclohexyl, 1,2,3-trimethylcycloheptyl, 1,2,4-trimethylcyclopentyl, 1,2,4-trimethylcyclohexyl, 1,2,4-trimethylcycloheptyl, 1,2,5-trimethylcyclopentyl, 1,2,5-trimethylcyclohexyl, 1,2,5-trimethylcycloheptyl, 1,2,6-trimethylcyclohexyl, 1,2,6-trimethylcycloheptyl, 1,2,7-trimethylcycloheptyl, 2,3,4-trimethylcyclopentyl, 2,3,4-trimethylcyclohexyl, 2,3,4-trimethylcycloheptyl, 2,3,5-trimethylcyclopentyl, 2,3,5-trimethylcyclohexyl, 2,3,5-trimethylcycloheptyl, 2,3,6-trimethylcyclohexyl, 2,3,6-trimethylcycloheptyl, 2,3,7-trimethylcycloheptyl, 3,4,4-trimethylcyclohexyl, 3,4,4-trimethylcyclopentyl, 2,2,5,5-tetramethylcyclopentyl, 2,2,5,5-tetramethylcyclohexyl, 2,2,5,5-tetramethylcycloheptyl, 2,2,6,6-tetramethylcyclohexyl, 2,2,6,6-tetramethylcycloheptyl, 2,2,7,7-tetramethylcycloheptyl, 2,2,4,4-tetramethylcyclopentyl, 2,2,4,4-tetramethylcyclohexyl, 2,2,4,4-tetramethylcycloheptyl, 2,2,3,3-tetramethylcyclopentyl, 2,2,3,3-tetramethylcyclohexyl, 2,2,3,3-tetramethylcycloheptyl, 3,3,4,4-tetramethylcyclopentyl, 3,3,4,4-tetramethylcyclohexyl, 3,3,4,4-tetramethylcycloheptyl, 3,3,5,5-tetramethylcyclohexyl, 3,3,5,5-tetramethylcycloheptyl, 1,2,3,4-tetramethylcyclopentyl, 1,2,3,4-tetramethylcyclohexyl, 1,2,3,4-tetramethylcycloheptyl, 1,2,3,5-tetramethylcyclopentyl, 1,2,3,5-tetramethylcyclohexyl, 1,2,3,5-tetramethylcycloheptyl, 1,2,3,6-tetramethylcyclohexyl, 1,2,3,6-tetramethylcycloheptyl, 2,3,4,5-tetramethylcyclopentyl, 2,3,4,5-tetramethylcyclohexyl, 2,3,4,5-tetramethylcycloheptyl, 2,3,4,6-tetramethylcycloheptyl, 2,3,4,6-tetramethylcyclohexyl, 2,3,4,7-tetramethylcycloheptyl, 2,2,3,4-tetramethylcyclopentyl, 2,2,3,4-tetramethylcyclohexyl, 2,2,3,4-tetramethylcycloheptyl, 2,2,3,5-tetramethylcyclopentyl, 2,2,3,5-tetramethylcyclohexyl, 2,2,3,5-tetramethylcycloheptyl, 2,2,3,6-tetramethylcyclohexyl, 2,2,3,6-tetramethylcycloheptyl, 2,2,3,7-tetramethylcycloheptyl, 2,3,3,4-tetramethylcyclohexyl, 2,3,3,4-tetramethylcyclopentyl, 2,3,3,4-tetramethylcycloheptyl, 2,3,3,5-tetramethylcyclopentyl, 2,2,3,5-tetramethylcyclohexyl, 2,3,3,5-tetramethylcycloheptyl, 2,3,3,6-tetramethylcyclohexyl, 2,3,3,6-tetramethylcycloheptyl, 2,3,3,7-tetramethylcycloheptyl, 2,3,3,4-tetramethylcyclopentyl, 2,2,3,4-tetramethylcyclohexyl, 2,3,3,4-tetramethylcycloheptyl, 2,2,3,5-tetramethylcyclopentyl, 2,2,3,5-tetramethylcyclohexyl, 2,2,3,6-tetramethylcyclohexyl, 2,2,3,6-tetramethylcycloheptyl, 2,2,3,7-tetramethylcycloheptyl, 2,2,4,5-tetramethylcyclopentyl, 2,2,4,5-tetramethylcyclohexyl, 2,2,4,5-tetramethylcycloheptyl, 2,2,4,6-tetramethylcyclohexyl, 2,2,4,6-tetramethylcycloheptyl, 2,2,4,7-tetramethylcycloheptyl, dicyclopropylmethyl, t-butylcyclopropylmethyl, t-butylcyclopentylmethyl, 2-isopropylcyclopentyl, 2-t-butylcyclopentyl, 2-isopropylcyclohexyl, 2-t-butylcyclopentyl, 2-isopropylcyclohexyl, 2-t-butylcyclohexyl, 2-t-amylcyclopentyl, t-amylcyclopropylmethyl, dicyclobutylmethyl, t-butylcyclobutylmethyl, 3-methylcycloheptylisopropyl, 2-methylcycloheptylisopropyl, 2-methylcyclohexylisopropyl, 2-methylcyclopentylisopropyl, etc.; cycloalkenes, e.g., cyclopentenyl, cyclohexenyl, cycloheptenyl, etc.; alkyl-substituted cycloalkenes, e.g., 1-methyl-3-cyclopentenyl, 1-methyl-3-cyclohexenyl, 1-methyl-3-cycloheptenyl, 1-methyl-4-cycloheptenyl, 3-cyclopentenylisopropyl, 3-cyclohexenylisopropyl, 3-cycloheptenylisopropyl, 4-cycloheptenylisopropyl, 3-cyclopentenylmethyl, 3-cyclopentenylmethyl, 3-cyclohexenylpropyl, 3-cyclohexenylethyl, 3-cycloheptenylpropyl, 3-cycloheptenylethyl, 4-cycloheptenylmethyl, 4-cycloheptenylethyl, 2-methyl-3-cyclohexenyl, 2-methyl-3-cyclopentenyl, 2-methyl-3-cycloheptenyl, 2-methyl-4-cycloheptenyl, 3-methyl-3-cyclohexenyl, 3-methyl-3-cyclopentenyl, 3-methyl-3-cycloheptenyl, 4-methyl-3-cycloheptenyl, 4-methyl-3-cyclohexenyl, 4-methyl-3-cyclopentenyl, 5-methyl-3-cyclopentenyl, 5-methyl-3-cyclohexenyl, 5-methyl-3-cycloheptenyl, 6-methyl-3-cyclohexenyl, 6-methyl-3-cycloheptenyl, 2-methyl-2-cyclopentenyl, 2-methyl-2-cyclohexenyl, 2-methyl-2-cycloheptenyl, 2-methyl-2-cyclopentenyl, 3-methyl-2-cyclohexenyl, 3-methyl-2-cycloheptenyl, 1-methyl-2-cyclopentenyl, 1-methyl-2-cyclohexenyl, 1-methyl-2-cycloheptenyl, 5-methyl-2-cyclohexenyl, 4-methyl-2-cyclopentenyl, 4-methyl-2-cycloheptenyl, 5-methyl-2-cyclohexenyl, 5-methyl-2-cycloheptenyl, 6-methyl-2-cyclohexenyl, 6-methyl-2-cycloheptenyl, 7-methyl-2-cycloheptenyl, 2,3-dimethyl-2-cyclopentenyl, 2,3-dimethyl-2-cyclohexenyl, 2,4-dimethyl-2-cyclopentenyl, 2,4-dimethyl-2-cyclohexenyl, 2,5-dimethyl-2-cyclohexenyl, 2,5-dimethyl-2-cycloheptenyl, 2,6-dimethyl-2-cyclohexenyl, 2,6-dimethyl-3-cyclohexenyl, 2,5-dimethyl-3-cyclohexenyl, 2,5-dimethyl-2-cyclopentenyl, 2,4-dimethyl-3-cyclopentenyl, 2,4-dimethyl-3-cyclohexenyl, 3,3-dimethyl-3-cyclopentenyl, 3,3-dimethyl-3-cyclohexenyl, 3,4-dimethyl-3-cyclopentenyl, 3,4-dimethyl-3-cyclohexenyl, 4,5-dimethylcyclo-3-pentenyl, 4,5-dimethyl-3-cyclo-3-hexenyl, 5,5-dimethyl-3-cyclohexenyl, 5,5-dimethyl-3-cyclopentenyl, 5,5-dimethyl-3-cycloheptenyl, 6,6-dimethyl-3-cyclohexenyl, 1,2-dimethyl-3-cyclopentenyl, 1,2-dimethyl-3-cyclohexenyl, 1,3-dimethyl-3-cyclopentenyl, 1,3-dimethyl-3-cyclohexenyl, 1,3-dimethyl-3-cycloheptenyl, 1,4-dimethyl-3-cyclopentenyl, 1,4-dimethyl-3-cyclohexenyl, 1,4-dimethyl-3-cyclohexenyl, 1,5-dimethyl-3-cyclopentenyl, 1,5-dimethyl-3-cyclohexenyl, 1,5-dimethyl-3-cycloheptenyl, 2,2,6-trimethyl-3-cyclohexenyl, 2,2,5-trimethyl-3-cyclohexenyl, 2,5,5-trimethyl-3-cyclohexenyl, 2,5,5-trimethyl-3-cyclopentenyl, 2,7,7-trimethyl-3-cycloheptenyl, 2,7,7-trimethyl-4-cycloheptenyl, 2,2,7-trimethyl-3-cycloheptenyl, 2,2,7-trimethyl-4-cycloheptenyl, 2,3,6-trimethyl-3-cyclohexenyl, 2,3,7-trimethyl-3-cycloheptenyl, 2,3,5-trimethyl-3-cyclopentenyl, 2,2,6,6-tetramethyl-3-cyclohexenyl, 2,2,5,5-tetramethyl-3-cyclopentenyl, 2,2,7,7-tetramethyl-3-cycloheptenyl, 2,3,5,5-tetramethyl-3-cyclopentenyl, 2,3,6,6-tetramethyl-3-cyclohexenyl, 2,3,7,7-tetramethyl-3-cycloheptenyl, 2,3,6,6-tetramethyl-3-cycloheptenyl, 2,3,5,5-tetramethyl-3-cyclohexenyl, 2,3,4,5-tetramethyl-3-cyclopentenyl, 2,3,4,5-tetramethyl-3-cyclohexenyl, etc; bicyclic compounds, such as norbornyl, norcaranyl, norpinanyl, bicyclo[2.2.2]octyl, etc.; alkyl substituted bicyclic compounds, e.g., 6,6-dimethyl-bicyclo[3.1.1]heptyl, 6,7,7-trimethylnorbornyl (bornyl or camphanyl), pinanyl, thujanyl, caranyl, fenchyl, 2-norbornylmethyl, etc.; unsubstituted and alkyl-substituted bicycloalkenes such as norbornenyl, norpinenyl, norcarenyl, 2-(4-norbornenyl)methyl, pinenyl, carenyl, fenchenyl, etc., and tricyclo compounds such as adamantyl and alkylsubstituted adamantyl, etc.

The preferred $R_1$ is cycloalkyl or bicycloalkyl or alkyl-substituted cycloalkyl or bicycloalkyl, especially where the alkyl group is in the $\beta$ or $\beta'$ positions. Further, preference exists for compounds in which $R_1$ is a cycloalkyl with two, three or four alkyl groups in the $\beta$, $\beta'$ positions such as $\beta$, $\beta$, $\beta'$, $\beta'$-tetraalkyl-substituted cyclopentyl, cyclobutyl, cyclohexyl, and cycloheptyl, as well as $\beta$, $\beta$, $\beta'$-trialkyl substituted cyclobutyl, cyclopropyl, cyclohexyl, cyclopentyl, and cycloheptyl, and fenchyl. Also preferred are $\beta$-alkylcycloalkyls in which the alkyl group is isopropyl or tertiary butyl.

These novel compounds are effective sweetness agents when used alone or in combination with other sweeteners in an ingesta, e.g., foodstuffs or pharmaceuticals. For example, other natural and/or artificial sweeteners which may be used with the novel compounds of the present invention include sucrose, fructose, corn syrup solids, dextrose, xylitol, sorbitol, mannitol, acetosulfam, thaumatin, invert sugar, saccharin, thiophene saccharin, meta-aminobenzoic acid, meta-hydroxybenzoic acid, cyclamate, chlorosucrose, dihydrochalcone, hydrogenated glucose syrups, aspartame (L-aspartyl-L-phenylalanine methyl ester) and other dipeptides, glycyrrhizin and stevioside and the like. These sweeteners when employed with the sweetness agents of the present invention, it is believed, could produce synergistic sweetness responses.

Furthermore, when the sweetness agents of the present invention are added to ingesta, the sweetness agents may be added alone or with nontoxic carriers such as the abovementioned sweeteners or other food ingredients such as acidulants and natural and artificial gums. Typical foodstuffs, and pharmaceutical preparations, in which the sweetness agents of the present invention may be used are, for example, beverages including soft drinks, carbonated beverages, ready to mix beverages and the like, infused foods (e.g. vegetables or fruits), sauces, condiments, salad dressings, juices, syrups, desserts, including puddings, gelatin and frozen desserts, like ice creams, sherbets, icings and flavored frozen desserts on sticks, confections, toothpaste, mouthwash, chewing gum, cereals, baked goods, intermediate moisture foods (e.g. dog food) and the like.

In order to achieve the effects of the present invention, the compounds described herein are generally added to the food product at a level which is effective to perceive sweetness in the food stuff and suitably is in an amount in the range of from about 0.0005 to 2% by weight based on the consumed product. Greater amounts are operable but not practical. Preferred amounts are in the range of from about 0.001 to about 1% of the foodstuff. Generally, the sweetening effect provided by the present compounds are experienced over a wide pH range, e.g. 2 to 10 preferably 3 to 7 and in buffered and unbuffered formulations.

It is desired that when the sweetness agents of this invention are employed alone or in combination with another sweetner, the sweetener or combination of sweeteners provide a sucrose equivalent in the range of from about 2 weight percent to about 40 weight percent and more preferably from about 3 weight percent to about 15 weight percent in the foodstuff or pharmaceutical.

A taste procedure for determination of sweetness merely involves the determination of sucrose equivalency. Sucrose equivalence for sweeteners are readily determined. The amount of a sweetener that is equivalent to a given weight percent sucrose can be determined by having a panel of tasters taste solutions of a sweetener at known concentrations and match its sweetness to standard solutions of sucrose.

In order to prepare compounds of the present invention, several reaction schemes may be employed. In one reaction scheme, compound I is prepared under art recognized amide forming conditions. Compounds of the general formula II (protected α-aminodicarboxylic acids) and III (substituted 2-amino acetamide) are reacted together to form compounds of formula IV. Subsequent removal of protecting groups B and Z from compounds of general formula IV give the desired compounds of general formula I:

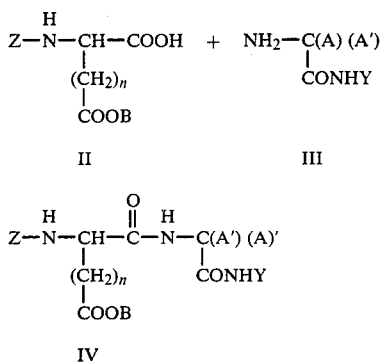

In these, group Z is an amino protecting group, B is a carboxyl protecting group, and A, A', Y, and n have the same meaning as previously described. A variety of protecting groups known in the art may be employed. Examples of many of these possible groups may be found in "Protective Groups in Organic Synthesis" by T. W. Green, John Wiley and Sons, 1981. Amond the preferred groups that may be employed are benzyloxycarbonyl for A and benzyl for B.

Coupling of compounds with general formula II to compounds having general formula III employs established techniques in peptide chemistry. One such technique uses dicyclohexylcarbodiimide (DCC) as the coupling agent. The DCC method may be employed with or without additives such as 4-dimethylaminopyridine or copper (II). The DCC coupling reaction generally proceeds at room temperature, however, it may be carried out from about $-20°$ to $50°$ C. in a variety of solvents inert to the reactants. Thus suitable solvents include, but are not limited to, N,N-dimethyl-formamide, methylene chloride, toluene and the like. Preferably the reaction is carried out under an inert atmosphere such as argon or nitrogen. Coupling usually is complete within 2 hours but may take as long as 24 hours depending on reactants.

Various other methods can be employed to prepare the desired compounds. The following illustrates such methods using aspartic acid as the amino dicarboxylic acid and serine as the amino monocarboxylic acid. Of course, other amino di- and monocarboxylic acids can be substituted for these exemplary acids.

For example, U.S. Pat. Nos. 3,786,039; 3,833,553; 3,879,372 and 3,933,781 disclose the reaction of N-protected aspartic anhydrides with amino acids and amino acid derivatives to yield the desired products. These N-protected aspartic anhydrides can be reacted with compounds of formula III by methods disclosed in the above patents. As described in U.S. Pat. No. 3,786,039 compounds of formula III can be reacted directly in inert organic solvents with L-aspartic anhydride having its amino group protected by a formyl, carbobenzyloxy, or p-methoxycarbobenzyloxy group which is subsequently removed after coupling to give compounds of general formula I. The N-acyl-L-aspartic anhydrides are prepared by reacting the corresponding acids with acetic anhydride in amounts of 1.0–1.2 moles per mole of the N-acyl-L-aspartic acid at $0°$ to $60°$ C. in an inert solvent. The N-acyl-L-aspartic anhydrides are reacted with preferably 1 to 2 moles of compounds of formula III in an organic solvent capable of dissolving both and inert to the same. Suitable solvents are, but not limited to, ethyl acetate, methyl propionate, tetrahydrofuran, dioxane, ethyl ether, N,N-dimethylformamide and benzene. The reaction proceeds smoothly at $0°$ to $30°$ C. The N-acyl group is removed after coupling by catalytic reaction proceeds smoothly at $0°$ to $30°$ C. The N-acyl group is removed after coupling by catalytic hydrogenation with palladium on carbon or with HBr or HCl in a conventional manner. U.S. Pat. No. 3,879,372 discloses that this coupling method can also be performed in an aqueous solvent at a temperature of $-10°$ to $50°$ C. and at a pH of 4–12.

Another method for the synthesis of the desired compounds is the reaction of compounds of formula III with suitable aspartic acid derivatives in which protecting groups have been attached to the amino and beta-carboxy groups and the alpha carboxy group has been converted to a reactive ester function. As disclosed in U.S. Pat. No. 3,475,403 these coupled products may be deprotected as described to yield the desired compounds of formula I.

An alternative scheme to the desired coupled compounds involves reaction of compounds of formula III with L-aspartic acid N-thiocarboxyanhydride by the method of Vinick and Jung, Tet. Lett., 23, 1315–18 (1982). An additional coupling method is described by T. Miyazawa, Tet Lett., 25, 771 (1984).

Compounds of general formula III, in which the amino groups are protected, synthesized using art recognized techniques. For example, compounds of formula III can be synthesized by standard amidation methods known in the art by reacting the free acid or acid functional equivalents, such as esters or anhydrides, with the corresponding amines under amide forming conditions, as for example in the presence of a coupling agent, such as dicyclohexylcarbodiimide. Reaction temperatures are in the range of $-78°$ C. to reflux. The reaction is carried out in a solvent that will dissolve both reactants and is inert to both as well. Solvents include, but are not limited to, methylene chloride, diethyl ether, tetrahydrofuran, dimethyl sulfoxide, dimethylformamide, and the like.

With regard to the removal of protecting groups from compounds of formula IV and N-protected precursors of formula III, a number of deprotecting techniques are known in the art and can be utilized to advantage depending on the nature of the protecting groups. Among such techniques is catalytic hydrogenation utilizing palladium on carbon or transfer hydrogenation with 1,4-cyclohexadiene. Generally the reaction is carried at room temperature but may be conducted from 5° to 65° C. Usually the reaction is carried out in the presence of a suitable solvent which may include, but are not limited to water, methanol, ethanol, dioxane, tetrahydrofuran, acetic acid, t-butyl alcohol, isopropanol or mixtures thereof. The reaction is usually run at a positive hydrogen pressure of 50 psi but can be conducted over the range of 20 to 250 psi. Reactions are generally quantitative taking 1 to 24 hours for completion.

In any of the previous synthetic methods the desired products are preferably recovered from reaction mixtures by crystallization. Alternatively, normal or reverse-phase chromatography may be utilized as well as liquid/liquid extraction or other means.

The desired compounds of formula I are usually obtained in the free acid form; they may also be recovered as their physiologically acceptable salts, i.e., the corresponding amino salts such as hydrochloride, sulfate, hydrosulfate, nitrate, hydrobromide, hydroiodide, phosphate or hydrophosphate; or the alkali metal salts such as the sodium, potassium, lithium, or the alkaline earth metal salts such as calcium or magnesium, as well as aluminum, zinc and the like salts.

Conversion of the free peptide derivatives of formula I into their physiologically acceptable salts is carried out by conventional means, as for example, bringing the compounds of formula I into contact with a mineral acid, an alkali metal hydroxide, an alkali metal oxide or carbonate or an alkaline earth metal hydroxide, oxide, carbonate or other complexed form.

These physiologically acceptable salts can also be utilized as sweetness agents usually having increased solubility and stability over their free forms.

It is known to those skilled in the art that the compounds of the present invention having asymmetric carbon atoms may exist in racemic or optically active forms. All of these forms are contemplated within the scope of the invention.

The compounds of the present invention have one asymmetric site, which is designated by an asterik (*) in the formula below, and one pseudoasymmetric site which is designated by a doulbe asterik (**):

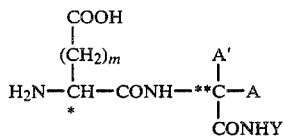

Whenever A is identical to A', the compounds of the present invention have only one asymmetric site, designated by the asterik, in the dicarboxylic acid moiety. Although both the D and L forms are possible; the preferred compounds are those in which the dicarboxylic acid group is in the L-configuration. Whenever, the groups A' and A are different the carbon atom designated by the double asteriks becomes an asymmetric center and the compounds of the present invention will contain at least two asymmetric centers. Regardless, the configuration around each of the asymmetric sites, whenever present, may exist in either the D or L forms, and all possible stereoisomers are contemplated to be within the scope of the present invention. Since the aspartyl group is in the L-configuration, whenever an asymmetric center is present at either of the other two carbon sites, the compounds of the present invention are diastereomers, which can be separated, if desired, by art-recognized techniques, as, for example, chromatography. However, mixtures of at least any two stereoisomers exhibit sweetness properties and are useful as sweeteners.

The following examples further illustrate the invention.

EXAMPLE 1

N-(L-Aspartyl)-N'-(2,2,5,5-tetramethyl-1-cyclopentyl)-2-methylalanine amide

To a stirred solution of N-Cbz-2-aminoisobutyric acid in dry $CH_2Cl_2$ containing dicyclohexylcarbodiimide and dimethylaminopyridine (DMAP), all at 0° C., is added, via an addition funnel, 2,2,5,5-tetramethyl-1-cyclopentyl amine dissolved in $CH_2Cl_2$. After stirring for 48 hours, the mixture is filtered, and the filtrate is washed with 5% HCl (1×50 ml), saturated $NaHCO_3$ (1×50 ml), and water (1×50 ml). The organic layer is separated, dried over $MgSO_4$ and is evaporated to yield N-Cbz-2-aminoisobutyric acid 2,2,5,5-tetramethylcyclopentyl amide.

N-Cbz-2-aminoisobutyric acid 2,2,5,5-tetramethylcyclopentyl amide is dissolved in $CH_3OH$ and is hydrogenated over 5% Pd/C in a Parr hydrogenation apparatus. When the reaction is complete the mixture is filtered through Celite and concentrated to yield 2-aminoisobutyric acid 2,2,5,5-tetramethylcyclopentyl amide.

To a magnetically stirred solution of 2-aminoisobutyric acid 2,2,5,5-tetramethylcyclopentyl amide in dry dimethylformamide at 0° C. under argon atmosphere is added N-Cbz-L-aspartic acid beta-benzyl ester followed by copper (II) chloride and dicyclohexylcarbodiimide. This is stirred for 18 hours, after which the reaction mixture is poured into 0.1N HCl and extracted with ethyl acetate. The organic phase is washed with saturated $NaHCO_3$ and then water, and dried over $MgSO_4$. Evaporation of the solvent yields N-(N'-Cbz-L-Aspartyl beta-benzyl ester)-2-aminoisobutyric acid 2,2,5,5-tetramethyl-1-cyclopentyl amide.

N-(N'-Cbz-L-Aspartyl beta-benzyl ester)-2-aminoisobutyric acid 2,2,5,5-tetramethyl-1-cyclopentyl amide is dissolved in $CH_3OH$ and hydrogenated over 5% Pd/C in a Parr apparatus. Upon completion of the reaction the mixture is filtered and concentrated to yield the final product.

Using the appropriate starting materials, these additional dipeptides are prepared:

N-L-Aspartyl-N'-(2,2,5-trimethylcyclopentyl)-2-methylalanine amide.

N-L-Aspartyl-N'-(2,5,dimethylcyclopentyl)-2-methylalanine amide.

N-L-Aspartyl-N'-fenchyl-2-methylalanine amide.

N-L-Aspartyl-N'-dicyclopropylmethyl-2-methylalanine amide.

N-L-Aspartyl-N'-(2-t-butylcyclopentyl)-2-methylalanine amide.

N-L-Aspartyl-N'-(1-t-butylcyclopropylmethyl)-2-methylalanine amide.

N-L-Aspartyl-N'-(1-isopropyl-1-cyclopropylmethyl)-2-methylalanine amide.

EXAMPLE 2

N-(L-Aspartyl-1-aminocyclopropyl-1-carboxylic acid N'-(2,2,5,5-tetramethylcyclopentyl)amide To a stirred solution of N-Cbz-1-aminocyclopropanecarboxylic acid in dry $CH_2Cl_2$ containing dicyclohexycarbodiimide and dimethylaminopyridine (DMAP), all at 0° C., is added, via an addition funnel, 2,2,5,5-tetramethyl-1-cyclopentyl amine dissolved in $CH_2Cl_2$. After stirring for 48 hours, the mixture is filtered, and the filtrate is washed with 5% HCl (1×50 ml), saturated $NaHCO_3$ (1×50 ml), and water (1×50 ml). The organic layer is separated, dried over $MgSO_4$ and evaporated to yield N-Cbz-1-aminocyclopropanecarboxylic acid 2,2,5,5-tetramethylcyclopentyl amide.

The N-Cbz-1-aminocyclopropanecarboxylic acid 2,2,5,5-tetramethylcyclopentyl amide is hydrogenated utilizing transfer hydrogenation. The above reaction is dissolved in absolute ethyl alcohol at 0° C. in an ultrasound bath. Palladium on carbon (10%) is added. The hydrogen source, 1,4-cyclohexadiene, is added and ultrasound is commenced for eight minutes. The slurry is then filtered through a bed of celite with ethyl alcohol. Rotary evaporation affords the free amine.

To a magnetically stirred solution of 1-aminocyclopropanecarboxylic acid 2,2,5,5-tetramethylcyclopentyl amide in dry dimethylformamide at 0° C. under argon atmosphere is added N-Cbz-L-aspartic acid beta-benzyl ester followed by copper (II) chloride and dicyclohexylcarbodiimide. This is stirred for 18 hours, after which the reaction mixture is poured into 0.1N HCl and extracted with ethyl acetate. The organic phase is washed with saturated $NaHCO_3$ and then water, and dried over $MgSO_4$. Evaporation of the solvent yields N-(N'-Cbz-L-Aspartyl beta-benzyl ester)-1-amino-1-cyclopropanecarboxylic acid 2,2,5,5-tetramethyl-1-cyclopentyl amide.

N-(N'-Cbz-L-Aspartyl beta-benzyl ester)-1-amino-1-cyclopropanecarboxylic acid 2,2,5,5-tetramethyl-1-cyclopentyl amide is hydrogenated utilizing transfer hydrogenation to afford the final product.

Using the appropriate starting materials, these additional dipeptides are prepared:

N-L-Aspartyl-1-aminocyclopropyl-1-carboxylic acid N-(2,2,5-trimethylcyclopentyl)amide.

N-L-Aspartyl-1-aminocyclopropyl-1-carboxylic acid N-(2,5-dimethylcyclopentyl)amide.

N-L-Aspartyl-1-aminocyclopropyl-1-carboxylic acid N-(dicyclopropylmethyl)amide.

N-L-Aspartyl-1-aminocyclopropyl-1-carboxylic acid N-(fenchyl)amide.

N-L-Aspartyl-1-aminocyclopropyl-1-carboxylic acid N-(2-t-butylcyclopentyl)amide.

N-L-Aspartyl-1-aminocyclopropyl-1-carboxylic acid N-(1-t-butyl-1-cyclopropylmethyl)amide.

N-L-Aspartyl-1-aminocyclopropyl-1-carboxylic acid N-(1-isopropyl-1-cyclopropylmethyl)amide.

EXAMPLE 3

N-L-Aspartyl-N'-(2,2,5,5-tetramethylcyclopentyl)-2-carbomethoxyglycine amide The above compound is prepared according to the procedure of Example 1, except N-Cbz-aminomalonic acid methyl ester is substituted for N-Cbz-2-aminoisobutyric acid.

Similarly, by utilizing the appropriate starting materials, the following additional compounds are prepared:

N-L-Aspartyl-N'-(2,2,5-trimethylcyclopentyl)-2-carbomethoxyglycine amide.

N-L-Aspartyl-N'-(2,5-dimethylcyclopentyl)-2-carbomethoxyglycine amide.

N-L-Aspartyl-N'-fenchyl-2-carbomethoxyglycine amide.

N-L-Aspartyl-N'-dicyclopropylmethyl-2-carbomethoxyglycine amide.

N-L-Aspartyl-N'-(2-t-butylcyclopentyl)-2-carbomethoxyglycine amide.

N-L-Aspartyl-N'-(1-t-butylcyclopropylmethyl)-2-carbomethoxyglycine amide.

N-L-Aspartyl-N'-(1-isopropyl-1-cyclopropylmethyl)-2-carbomethoxyglycine amide.

EXAMPLE 4

N-L-Aspartyl-N'-(2,2,5,5-tetramethylcyclopentyl)-2-carbomethoxyalanine amide The above compound is prepared according to the procedure in Example 1, except N-Cbz-2-amino-2-methylmalonic acid methyl ester is substituted for N-Cbz-2-aminoisobutyric acid.

Similarly, by utilizing the appropriate starting materials, the following additional compounds are prepared:

N-L-Aspartyl-N'-(2,2,5-trimethylcyclopentyl)-2-carbomethoxyalanine amide.

N-L-Aspartyl-N'-(2,5-dimethylcyclopentyl)-2-carbomethoxyalanine amide.

N-L-Aspartyl-N'-fenchyl-2-carbomethoxyalanine amide.

N-L-Aspartyl-N'-dicyclopropylmethyl-2-carbomethoxyalanine amide.

N-L-Aspartyl-N'-(2-t-butylcyclopentyl)-2-carbomethoxyalanine amide.

N-L-Aspartyl-N'-(1-t-butylcyclopropylmethyl)-2-carbomethoxyalanine amide.

N-L-Aspartyl-N'-(1-isopropyl-1-cyclopropylmethyl)-2-carbomethoxyalanine amide.

The compounds of this invention, possess greater stability than corresponding amides of the prior art. In addition, the present compounds lack a chiral center when A is other than a carbalkoxy group and are readily preparable and easily purified. The compounds wherein A is carbalkoxy, particularly carbomethoxy, are sweeter than corresponding amides of the prior art.

What is claimed is:

1. A composition comprising an edible composition and an effective sweetening amount of compound represented by the formula:

$$\begin{array}{c} \underline{L} \\ H_2N-CH-CONH-C(A')A \\ | \qquad\qquad\qquad | \\ (CH_2)_m \qquad\quad CONHY \\ | \\ CO_2H \end{array}$$

wherein

A is $CO_2R$ wherein R is alkyl containing 1–3 carbon atoms;

A' is hydrogen or alkyl containing 1–3 carbon atoms;

Y is $-(CHR_2)_n-R_1$ or $-CHR_3R_4$;

$R_1$ is cycloalkyl, cycloalkenyl, lower alkyl substituted cycloalkyl or cycloalkenyl, bicycloalkyl, bicycloalkenyl or tricycloalkyl containing up to 10 ring carbon atoms and up to a total of 12 carbon atoms;

$R_2$ is H or alkyl containing 1-4 carbon atoms;

$R_3$ and $R_4$ are each cycloalkyl containing 3-4 ring carbon atoms;

n is 0 or 1; and m is 0 or 1;

and food acceptable salts thereof.

2. The composition of claim 1 wherein $R_1$ in the compound is cyclopentyl or cyclohexyl containing a total of up to 10 carbon atoms.

3. The composition of claim 1 wherein n in the compound is 0.

4. The composition of claim 1 wherein $R_1$ in the compound is mono-, di-, tri or tetramethyl cycloalkyl or bicycloalkyl containing up to 10 carbon atoms.

5. The composition of claim 1 wherein $R_1$ in the compound is a β-methyl-substituted cycloalkyl or bicycloalkyl.

6. The composition of claim 1 wherein $R_1$ in the compound is a β,β or β,β'-dimethyl-substituted cycloalkyl or bicycloalkyl.

7. The composition of claim 1 wherein $R_1$ in the compound is a β,β,β'-trimethyl-substituted cycloalkyl or bicycloalkyl.

8. The composition of claim 1 wherein $R_1$ in the compound is a β,β,β',β'-tetramethyl-substituted cycloalkyl or bicycloalkyl.

9. The composition of claim 1 wherein $R_3$ and $R_4$ in the compound are cyclopropyl.

10. The composition of claim 1 wherein the compound is N-L-Aspartyl-N'-(2,2,5,5-tetramethylcyclopentyl)-2-carbomethoxyglycine amide.

11. The composition of claim 1 wherein the compound is N-L-Aspartyl-N'-(2,2,5-trimethylcyclopentyl)-2-carbomethoxyglycine amide.

12. The composition of claim 1 wherein the compound is N-L-Aspartyl-N'-(2,5-dimethylcyclopentyl)-2-carbomethoxyglycine amide.

13. The composition of claim 1 wherein the compound is N-L-Aspartyl-N'-fenchyl-2-carbomethoxyglycine amide.

14. The composition of claim 1 wherein the compound is N-L-Aspartyl-N'-dicyclopropylmethyl-2-carbomethoxyglycine amide.

15. The composition of claim 1 wherein the compound is N-L-Aspartyl-N'-(2-t-butylcyclopentyl)-2-carbomethoxylglycine amide.

16. The composition of claim 1 wherein the compound is N-L-Aspartyl-N-'-(1-t-butylcyclopropylmethyl)-2-carbomethoxyglycine amide.

17. The composition of claim 1 wherein the compound is N-L-Aspartyl-N'-(1-isopropyl-1-cyclopropylmethyl)-2-carbomethoxyglycine amide.

18. The composition of claim 1 wherein the compound is N-L-Aspartyl-N'-(2,2,5,5-tetramethylcyclopentyl)-2-carbomethoxyalanine amide.

19. The composition of claim 1 wherein the compound is N-L-Aspartyl-N'-(2,2,5-trimethylcyclopentyl)-2-carbomethoxyalanine amide.

20. The composition of claim 1 wherein the compound is N-L-Aspartyl-N'-(2,5-dimethylcyclopentyl)-2-carbomethoxyalanine amide.

21. The composition of claim 1 wherein the compound is N-L-Aspartyl-N'-fenchyl-2-carbomethoxyalanine amide.

22. The composition of claim 1 wherein the compound is N-L-Aspartyl-N'-dicyclopropylmethyl-2-carbomethoxyalanine amide.

23. The composition of claim 1 wherein the compound is N-L-Aspartyl-N'-(2-t-butylcyclopentyl)-2-carbomethoxyalanine amide.

24. The composition of claim 1 wherein the compound is N-L-Aspartyl-N'-(1-t-butylcyclopropylmethyl)-2-carbomethoxyalanine amide.

25. The composition of claim 1 wherein the compound is N-L-Aspartyl-N'-(1-isopropyl-1-cyclopropylmethyl)-2-carbomethoxyalanine amide.

* * * * *